United States Patent
Routh, Jr. et al.

(10) Patent No.: US 9,281,163 B2
(45) Date of Patent: Mar. 8, 2016

(54) HIGH CAPACITY TEM GRID

(71) Applicant: FEI Company, Hillsboro, OR (US)

(72) Inventors: Brian Roberts Routh, Jr., Beaverton, OR (US); Valerie Brogden, Portland, OR (US); Michael Schmidt, Gresham, OR (US)

(73) Assignee: FEI Company, Hillsboro, OR (US)

( * ) Notice: Subject to any disclaimer, the term of this patent is extended or adjusted under 35 U.S.C. 154(b) by 0 days.

(21) Appl. No.: 14/251,739

(22) Filed: Apr. 14, 2014

(65) Prior Publication Data

US 2015/0294834 A1 Oct. 15, 2015

(51) Int. Cl.
*H01J 37/20* (2006.01)
*H01J 37/26* (2006.01)
*G01N 1/44* (2006.01)

(52) U.S. Cl.
CPC . *H01J 37/20* (2013.01); *G01N 1/44* (2013.01); *H01J 37/26* (2013.01); *H01J 37/261* (2013.01); *H01J 2237/08* (2013.01); *H01J 2237/201* (2013.01); *H01J 2237/204* (2013.01); *H01J 2237/2007* (2013.01); *H01J 2237/2602* (2013.01); *H01J 2237/31745* (2013.01)

(58) Field of Classification Search
CPC .............. H01J 37/20; H01J 2237/201; H01J 2237/208; H01J 2237/31745; H01J 2237/2007; H01J 2237/31749; H01J 2237/1532; H01J 2237/20
See application file for complete search history.

(56) References Cited

U.S. PATENT DOCUMENTS

| | | | | |
|---|---|---|---|---|
| 6,420,722 | B2 * | 7/2002 | Moore et al. | 250/559.27 |
| 7,423,263 | B2 * | 9/2008 | Hong et al. | 250/304 |
| 8,729,469 | B1 * | 5/2014 | Schmidt et al. | 250/309 |
| 8,766,214 | B2 | 7/2014 | Routh, Jr. et al. | |
| 8,822,921 | B2 | 9/2014 | Schmidt et al. | |
| 2004/0129878 | A1 * | 7/2004 | Tomimatsu et al. | 250/307 |
| 2005/0199810 | A1 * | 9/2005 | Hiller et al. | 250/311 |
| 2005/0230636 | A1 * | 10/2005 | Tanaka et al. | 250/440.11 |
| 2006/0189021 | A1 * | 8/2006 | Iwasaki | H01J 37/20 438/48 |
| 2009/0212228 | A1 * | 8/2009 | Hirose et al. | 250/396 R |
| 2012/0006711 | A1 * | 1/2012 | Goodman et al. | 206/456 |
| 2012/0135260 | A1 * | 5/2012 | Jang et al. | 428/546 |
| 2013/0214468 | A1 * | 8/2013 | Giannuzzi | 269/287 |
| 2013/0248354 | A1 | 9/2013 | Keady et al. | |
| 2013/0319849 | A1 | 12/2013 | Fuller et al. | |
| 2014/0197311 | A1 * | 7/2014 | Nederlof | 250/307 |

FOREIGN PATENT DOCUMENTS

CN 103646839 A * 3/2014 ............ H01J 37/20

OTHER PUBLICATIONS

Ayache, Jeanne, et al., "A Guide to Sample Preparation Methods for TEM in Materials Science and Biology," Microscopy and Analysis, 2009, pp. 11-13.
Unknown, "Tilted Attachment of Lamella to Notched Sample Grid", IP.com; Jan. 14, 2009.
Unknown, "High Density Sample Preparation", IP.com; Dec. 7, 2012.

* cited by examiner

*Primary Examiner* — Michael Logie
(74) *Attorney, Agent, or Firm* — Scheinberg & Associates, PC; Michael O. Scheinberg; Nathan H. Calvert

(57) ABSTRACT

A TEM grid provides posts having steps, the steps increasing the number of samples that can be attached to the grid. In some embodiments, each post includes a one sided stair step configuration. A method of extracting multiple samples includes extracting samples and attaching the samples to the different stair steps on the posts.

24 Claims, 7 Drawing Sheets

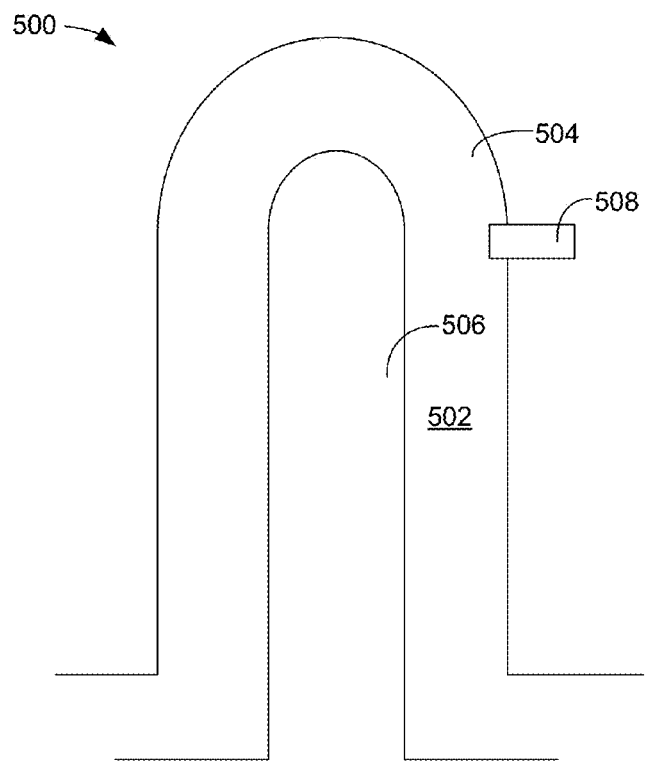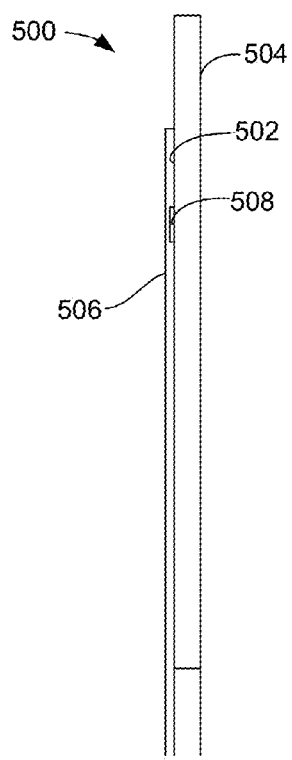
FIG. 5A (Prior Art)
FIG. 5B (Prior Art)
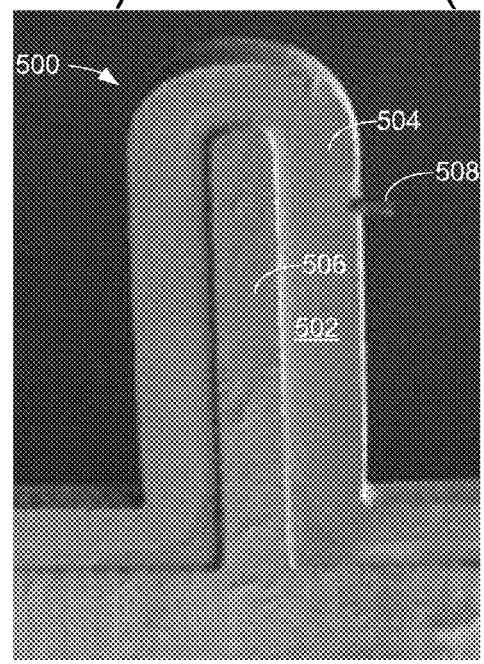
FIG. 5C (Prior Art)

HIGH CAPACITY TEM GRID

TECHNICAL FIELD OF THE INVENTION

The present invention relates to a transmission electron microscope (TEM) grid and to the extraction and handling of samples for observation using transmission electron microscopes and scanning transmission electron microscopes.

BACKGROUND OF THE INVENTION

Nanotechnology, materials science, and life sciences demand the ability to form images at nanometer scale resolution. For example, integrated circuits are now manufactured with features as small as a few tens of nanometers, and the development and control of integrated circuit manufacturing processes requires forming useful images of such feature. Variations in the lithography processes used to make integrated circuit necessitate continually monitoring or measuring the process results to ensure that the product parameters remain within acceptable ranges.

The importance of such monitoring increases considerably as minimum feature sizes approach the limits of resolution of the lithographic process. Features to be monitored may include the width and spacing of interconnecting lines, spacing and diameter of contact holes, and the surface geometry such as corners and edges of various features. Features on a semiconductor wafer are three-dimensional structures and a complete characterization must describe not just a surface dimension, such as the top width of a line or trench, but a three-dimensional profile of the feature. It is also necessary analyze contamination and other defects that are found in the fabrication process.

Some observations and measurements can be made using a scanning electron microscope (SEM). In an SEM, a primary electron beam is focused to a fine spot that scans the surface to be observed. Secondary electrons are emitted from the surface as it is impacted by the primary beam. The secondary electrons are detected, and an image is formed, with the brightness at each point of the image being determined by the number of secondary electrons detected when the beam impacts a corresponding spot on the surface. As features to be observed continue to get smaller and smaller, however, there comes a point where the features to be measured are too small for the resolution provided by an ordinary SEM.

Transmission electron microscopes (TEMs) allow observers to see extremely small features, on the order of nanometers. In contrast to SEMs, which only image the surface of a material, TEMs also allows analysis of the internal structure of a sample. In a conventional TEM, a broad beam impacts the sample that is held in a holder referred to as a "TEM grid" and electrons that are transmitted through the sample are focused to form an image. The sample must be sufficiently thin to allow many of the electrons in the primary beam to travel though the sample and exit on the opposite site. TEM samples are typically less than 100 nm thick.

In a scanning transmission electron microscope (STEM), a primary electron beam is focused to a fine spot, and the spot is scanned across the sample surface. Electrons that are transmitted through the work piece are collected by an electron detector on the far side of the sample, and the intensity of each point on the image corresponds to the number of electrons collected as the primary beam impacts a corresponding point on the surface.

Because a sample must be very thin for viewing with transmission electron microscopy (whether TEM or STEM), preparation of the sample can be delicate, time-consuming work. The term "TEM" as used herein refers to a TEM or an STEM, and references to preparing a sample for a TEM are to be understood to also include preparing a sample for viewing on an STEM.

The term "substrate" is used herein to refer to the work piece from which the sample is extracted, and the term "sample" will be used to describe the portion of the substrate that is extracted from the substrate and mounted onto a TEM grid for thinning and/or for observation.

Several techniques are used for preparing TEM specimens. These techniques may involve cleaving, chemical polishing, mechanical polishing, or broad beam, low energy ion milling, or combining one or more of the above. The disadvantage to these techniques is that they often require that the starting material be sectioned into smaller and smaller pieces, thereby destroying much of the original work piece.

Other techniques, generally referred to as "lift-out" techniques, use a focused ion beam to cut the sample from a substrate or bulk sample so that it can be lifted out without destroying or damaging surrounding parts of the substrate. Such techniques are useful in analyzing the results of processes used in the fabrication of integrated circuits, as well as in analyzing materials in the physical or biological sciences. These techniques can be used to form samples from any orientation within the substrate (e.g., either in cross-section or in plan view). Some lift-out techniques extract a sample in the form of a lamella sufficiently thin for use directly in a TEM; other lift-out techniques extract a "chunk" or large sample that requires additional thinning before observation. The sample may be thinned while still attached to the substrate, while attached to a probe used to transport the sample from the substrate to the TEM grid, or after it is attached to the TEM grid. The lamella may be formed as a uniformly thin structure or it may include a thin viewing area within a thicker support structure. An extracted lamella typically forms a sample oriented normal to the substrate surface. A chunk is often extracted to form a sample parallel to the substrate surface as described in U.S. Pat. No. 7,423,263 to Hong et al. for "Planar View Sample Preparation," which is owned by the applicant of the present invention and which is hereby incorporated by reference.

Techniques in which the prepared sample is extracted from the substrate and moved to a TEM grid within the focused ion beam (FIB) system vacuum chamber are commonly referred to as "in-situ" techniques. Techniques in which the sample is formed by a focused ion beam and then the substrate is removed from the vacuum chamber before the sample is removed from the substrate are call "ex-situ" techniques.

In one technique, samples are thinned to the desired thickness before they are separated from the substrate and the samples are transferred to a metallic grid covered with a thin electron transparent film. The sample is viewed by passing an electron beam through the sample as it rests on the film. FIG. 1 shows a prior art TEM grid 100, which is typically made of copper, nickel, or gold. Although dimensions can vary, a typical grid might have, for example, a diameter of 3.05 mm and have a middle portion 102 consisting of cells 104 of size 90 µm×90 µm defined by bars 106 which have a width of 35 µm. The electrons in an impinging electron beam will be able to pass through the cells 104, but will be blocked by the bars 106. The middle portion 102 is surrounded by an edge portion 108. The width of the edge portion 108 is 0.225 mm. The edge portion 108 has no cells and displays an orientation mark 110. The electron transparent support film is approximately 20 nm thick and uniform across the entire sample carrier. TEM specimens to be analyzed are placed or mounted within cells 104.

To remove the sample from the substrate, a probe attached to the micromanipulator is positioned over the sample and carefully lowered to contact it. For ex-situ removal, the probe can use a vacuum, electrostatic forces, or an adhesive to attach the sample to the probe tip to move it from the substrate to the grid. One such system for ex-situ extraction of samples is described in U.S. Pat. No. 8,357,913 to Agorio et al. for "Method and Apparatus for Sample Extraction and Handling."

Rather than thinning the sample before it is removed from the substrate, in some in-situ processes samples are removed from the substrate using a probe connected to a micromanipulator and attached to a post (also referred to as a "tooth" or "finger") of a TEM grid such as the one shown in FIG. 2. The partly or fully formed sample is typically attached to a probe by beam-induced deposition after it is formed. The sample is then separated from the substrate and transported by the probe to a TEM grid, where is it attached by beam-induced deposition to a post. The connection between the probe and the sample is then severed, leaving the sample on the TEM grid post. The sample probe may be rotated and the TEM grid may be tilted or rotated to ensure that the sample is attached to the post in the desired orientation for processing an viewing. Techniques for forming and extracting samples are described, for example, in U.S. Pat. Pub. No. 2013/0248354 for "High Throughput TEM Preparation processes and Hardware for Backside Thinning of Cross-Sectional View Lamella" by Keady et al. and in WO2012/103534 for "TEM Sample Preparation" of Blackwood et al., both of which are owned by the applicant of the present application and are hereby incorporated by reference.

A typical post-type TEM grid 200 comprises a portion of a 3 mm circle. In some applications, samples, such as sample 202A, 202B, and 202C, are attached to posts 204A, 204B, 204C, or 204D of the TEM grid 200 by ion beam deposition or an adhesive. The sample extends from the post so that an electron beam in a TEM (not shown) will have a free path through the sample to a detector under the sample. The sample is typically mounted with the thin viewing area parallel to the plane of the TEM grid, and the TEM grid is mounted so that the plane of the TEM grid is perpendicular to the electron beam when the sample is observed. FIG. 3 shows another TEM grid 300 having posts 302A and 302B to which samples 304A, 304B, 304C, and 304D are attached. The posts of TEM grid 300 have a different shape than the posts of TEM grid 200.

FIGS. 5A-5C show enlarged views of a post 500 of a typical prior art TEM grid. The TEM post typically includes a shelf 502 referred to as a "setback." FIG. 5A illustrates a front-view of the post 500 showing the shelf 502 formed by an outer edge 504 that is thinner than the interior portion 506 of post 500. The setback facilitates attachment of the sample 508 to the post 500 and minimizes or avoids damage to the TEM grid during attachment. The shelf 502 may run continuously around the perimeter of the entire TEM post. FIG. 5B illustrates a side-view of the post 500 FIG. 5A. FIG. 5C is a photomicrograph showing a TEM post 500 having a shelf 502. The thinner outer edge 504 extends along the entire post 500 and between posts.

Although, the setback is not shown in FIGS. 2, 3, 4A, 4B, 8A, and 8B, it should be recognized that the TEM grids of each have a setback on which the sample or lamella is attached to. The setback is not shown for clarity purposes in these other figures.

The term TEM grid is used herein to refer to any structure onto which the sample is mounted including not only a metallic grid covered with a thin electron transparent film as shown in FIG. 1, but also post-type grids as shown in FIGS. 2 and 3, as well as any other type of support, such as a wire to which samples can be attached. The TEM grid is typically mounted in a TEM sample holder. The sample holder can be removed from the ion beam system vacuum chamber to transport the TEM grid with the samples to a TEM for viewing. Sample holders for holding TEM grids and systems for transporting sample holders are known.

Preparation of TEM samples using prior art methods of sample extraction are time consuming. Critical Dimension ("CD") metrology and other process monitoring techniques often requires multiple samples from different locations on a wafer to sufficiently characterize and qualify a specific process. In some circumstances, for example, it will be desirable to analyze from 15 to 50 TEM samples from a given wafer. When so many samples must be extracted and measured, the total time to process the samples from one wafer can be days or even weeks. Even though the information that can be discovered by TEM analysis can be very valuable, the entire process of creating and measuring TEM samples has historically been so labor intensive and time consuming that it has not been practical to use this type of analysis for manufacturing process control.

Speeding up the process of sample extraction and transfer would provide significant time savings by allowing a semiconductor wafer to be more rapidly returned to the production line. Automating the lift out process will increase the number of samples extracted by the ion beam system in a given time period.

SUMMARY OF THE INVENTION

An object of the invention is to provide improved TEM grids for samples used in transmission electron microscopy and to provide methods to facilitate TEM sample production.

Embodiments of the invention provide a TEM grid that includes a post having a jagged edge to provide steps that form sample positions for mounting multiple samples on each post. The TEM grid facilitates automated sample prep by accommodating more samples than a prior art TEM grid. Preferably, machine-readable identification marks on each step facilitate automatic sample preparation.

The foregoing has outlined rather broadly the features and technical advantages of the present invention in order that the detailed description of the invention that follows may be better understood. Additional features and advantages of the invention will be described hereinafter. It should be appreciated by those skilled in the art that the conception and specific embodiments disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims.

BRIEF DESCRIPTION OF THE DRAWINGS

For a more thorough understanding of the present invention, and advantages thereof, reference is now made to the following descriptions taken in conjunction with the accompanying drawings, in which:

FIGS. 5A-5C shows an enlarged view of a post of a TEM grid.

DETAILED DESCRIPTION OF PREFERRED EMBODIMENTS

Some embodiments of the invention provide TEM grids that provide increased sample capacity. A staircase-type post design of some embodiments increases the number of samples that can be attached to a TEM grid by minimizing wasted space below the welded samples on each post.

In some embodiments, a one-sided staircase structure optimizes a technique for inverted lift-out, as described in U.S. Pat. Pub. No. 2013/0248354 for "High Throughput TEM Preparation processes and Hardware for Backside Thinning of Cross-Sectional View Lamella" by Keady et al., by locating all sample positions on the side of the grid on which it is easiest to weld.

In some embodiments, the staircase design, one-sided or two-sided, is combined with the machine and/or human readable indicia, such as simplified letters or geometric shapes, at the top of each staircase and/or on each stair step to allow for rapid and accurate location and identification of sample locations.

The asymmetry of a one-sided staircase makes it easy for an operator to correctly orient the grid properly when loading it in the grid holder. This facilitates accurate machine-vision driven placement of sample. The non-staircase side of the post provides for very low redeposition thinning of the sample, which allows for fine energy dispersive x-ray spectroscopy analysis. For example, on a one-sided staircase that extends to the right, the left side of the posts allows the user to place a sample a great distance from the bulk of the supporting grid. This can be advantageous when the user wishes to perform a spectroscopic analysis and wishes to minimize the risk of redeposition from the grid fouling the results. This is particularly important when looking for copper or the absence of copper since the grid may be made of copper, and unintended sputtered of cooper from the grid can redeposit onto the sample contaminating it.

Figure 8A:
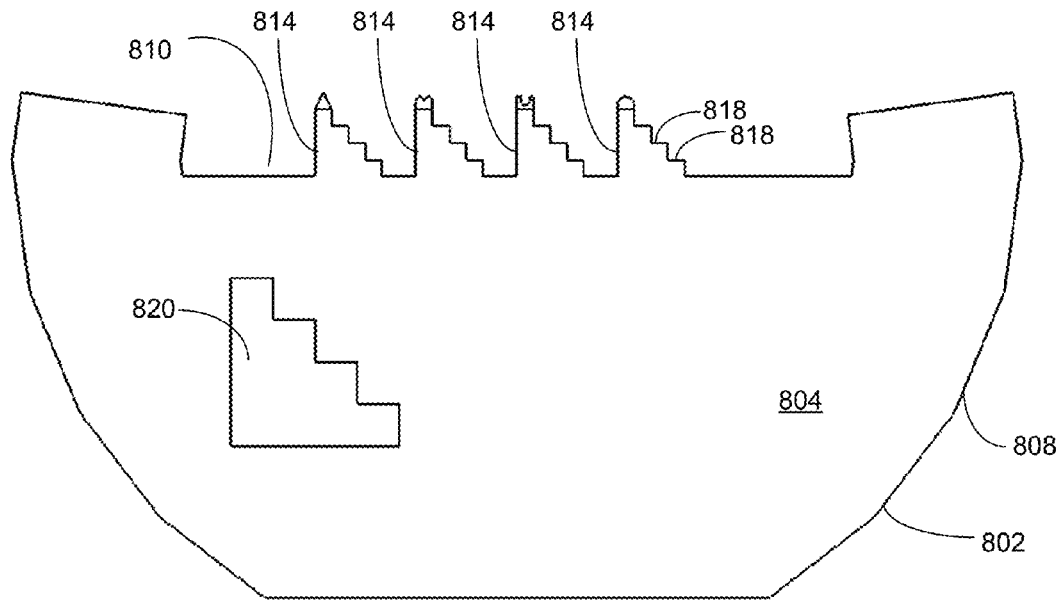
FIGS. 8A and 8B show, respectively, a front view and a rear view of a preferred embodiment of a TEM grid.
Figure 8B:
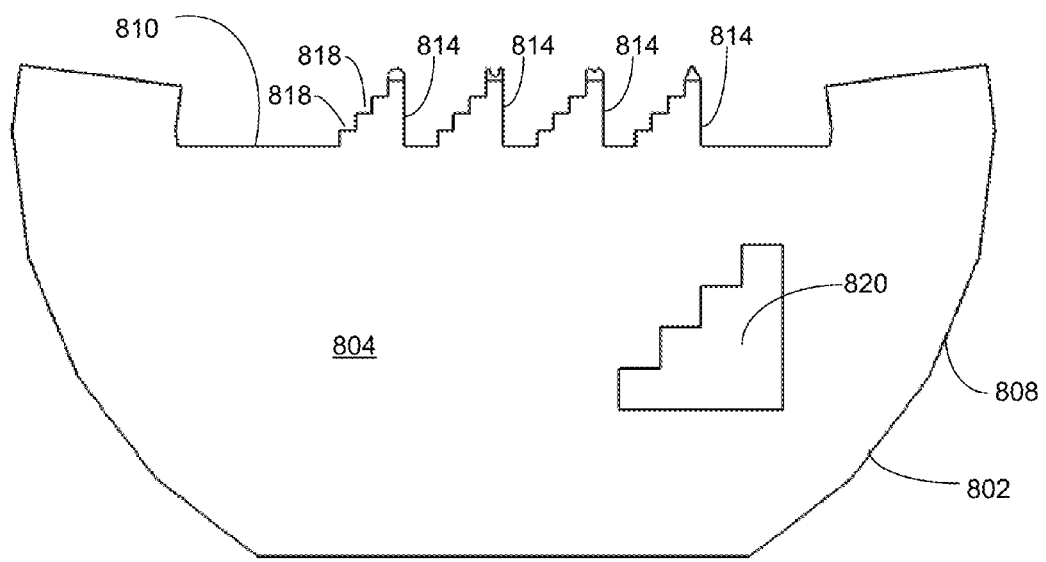

Depending on the specific implementation, the design of the grid can be varied to change the size and number of the steps on each post, as well as the number of posts, to increase capacity or provide more space for manipulation of the sample. Some applications require small numbers of large samples, while other application require large numbers of small samples, and the grid design can be varied to accommodate the specific requirements of each application. For example, in some applications, very large "chunk" samples, that is, samples having dimensions of greater than 100 µm on a side, are extracted. The large chunks may be extracted, for example, by using the Vion Plasma FIB from FEI Company, Hillsboro, Oreg., the assignee of the present application. These large samples are preferably attached to grids that have a smaller number of available positions, such as having a smaller number of steps on each post and/or having a smaller number of posts. These large samples are typically used in activities that are typically not high-throughput, and so using multiple grids with fewer sample mounted on each grid is not a problem. STEM metrology processes, on the other hand, typically require a large number of samples, and the ability to reliably and rapidly obtain a large number of sample is more important in this application. In such applications, grids having more posts with smaller and more steps on each post would allow more lamella per grid, and minimizing grid load-and-unload cycles could save time. Simplified identifying letters could be replaced with other geometric shapes to aid in machine vision recognition or grid manufacturability. The tops of different posts can be formed into different geometric shapes to facilitate identification of each post as shown in FIGS. 8A and 8B.

Providing indicia on the top of each staircase that are easily located using machine vision facilitates automated lift-out processes. It also facilitates an automated routine to locate a specific grid and determine the orientation of the grid by fitting a line to the locations of each staircase. This would allow for automatic rotation adjustment to compensate for any orientation error in loading the grid into a grid holder, which error can easily be 2-3 degrees when manually loading the grids. The stage rotation can also be left in its original position, and instead, the measured grid rotation is used to help drive to each position more accurately. This saves time in re-finding the grid. The automatic rotation adjustment can be performed prior to welding the lamella to the grid if it is critical that the lamella is lined up with the finger or post. By noting the orientation of the grid, the orientation of the grid can be driven back to the adjusted rotation.

Figure 1:
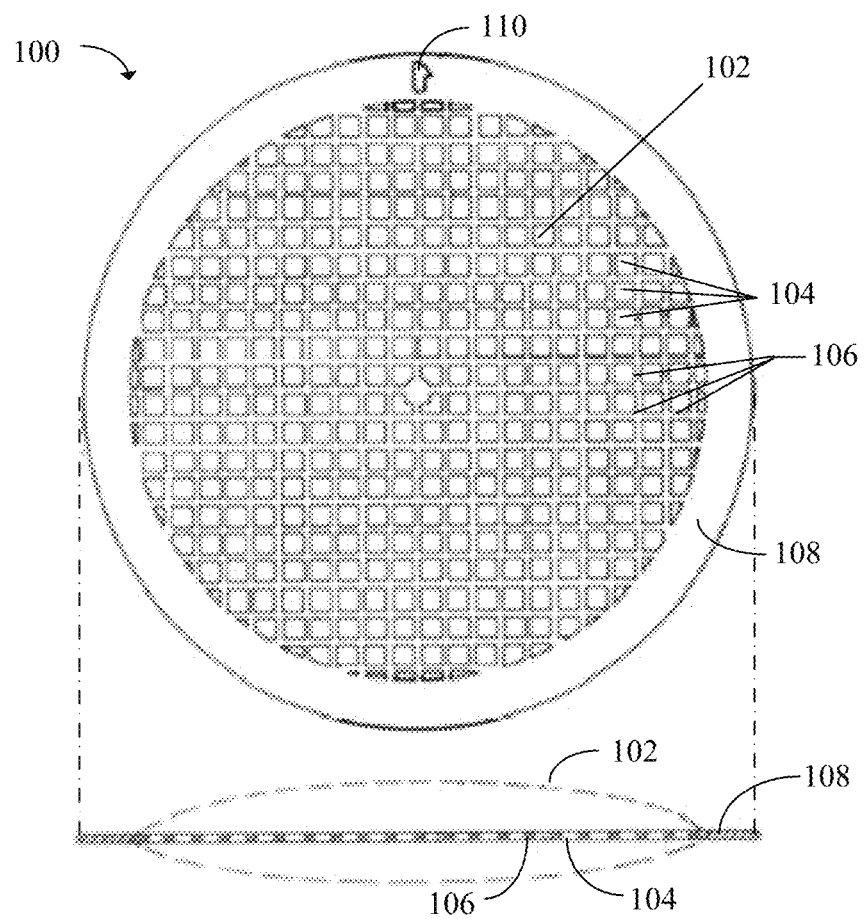
FIG. 1 shows a first type of prior art TEM grid.
Figure 2:
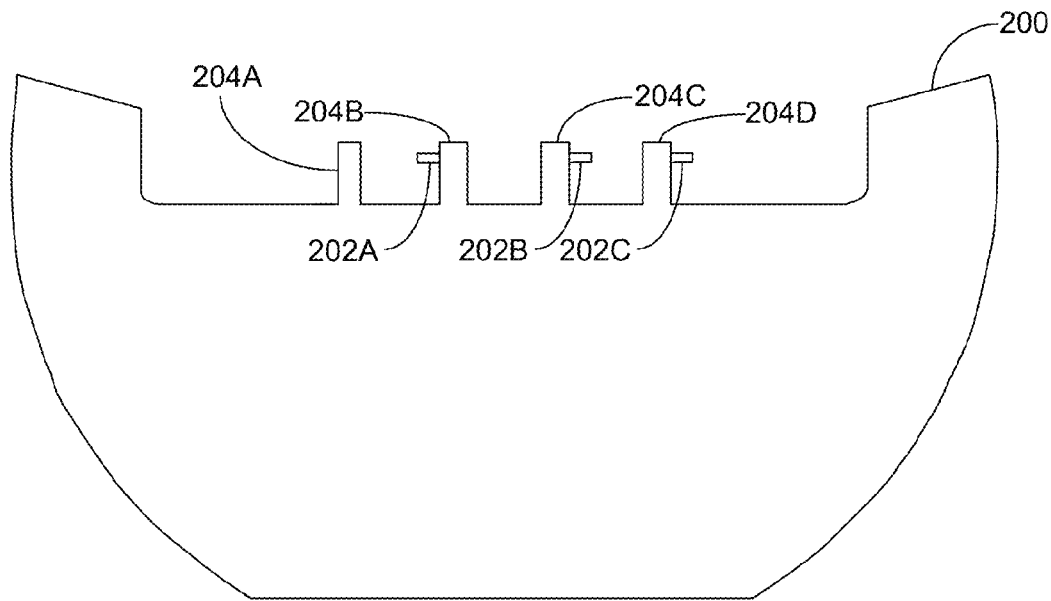
FIG. 2 shows a second type of prior art TEM grid.
Figure 3:
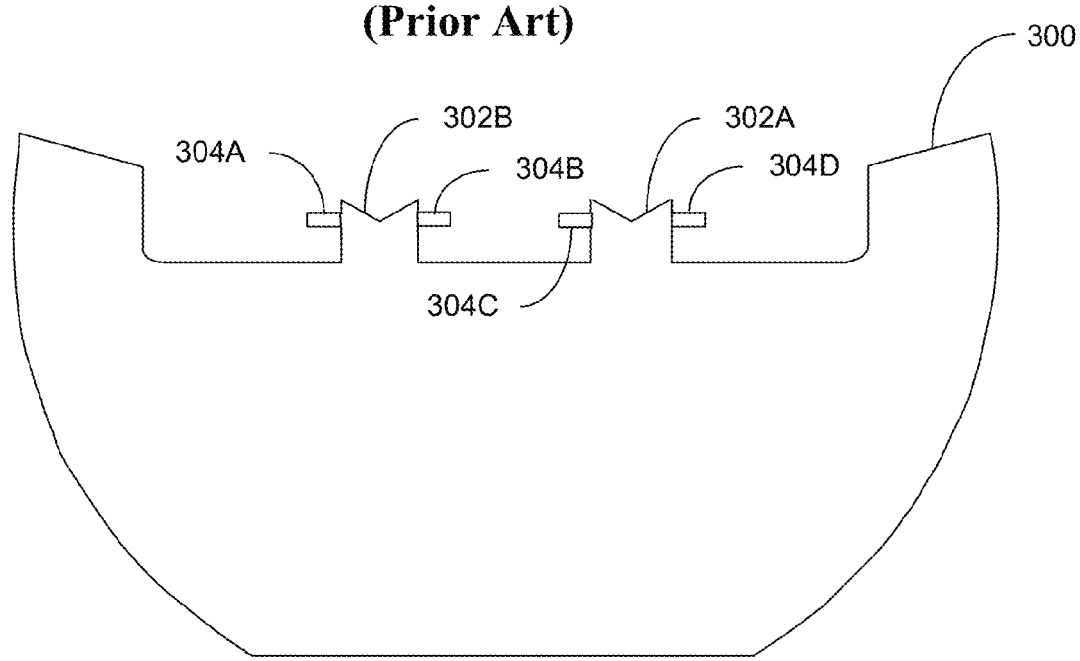
FIG. 3 shows a third type of prior art TEM grid.
Figure 4A:
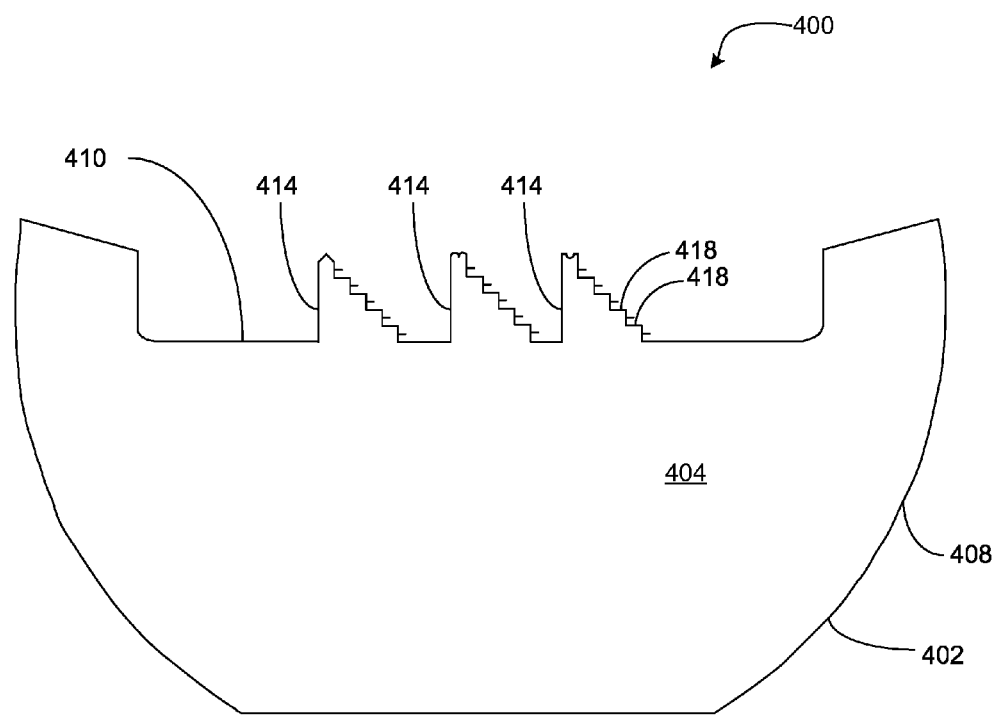
FIGS. 4A and 4B show an embodiment of a TEM grid.
Figure 4B:
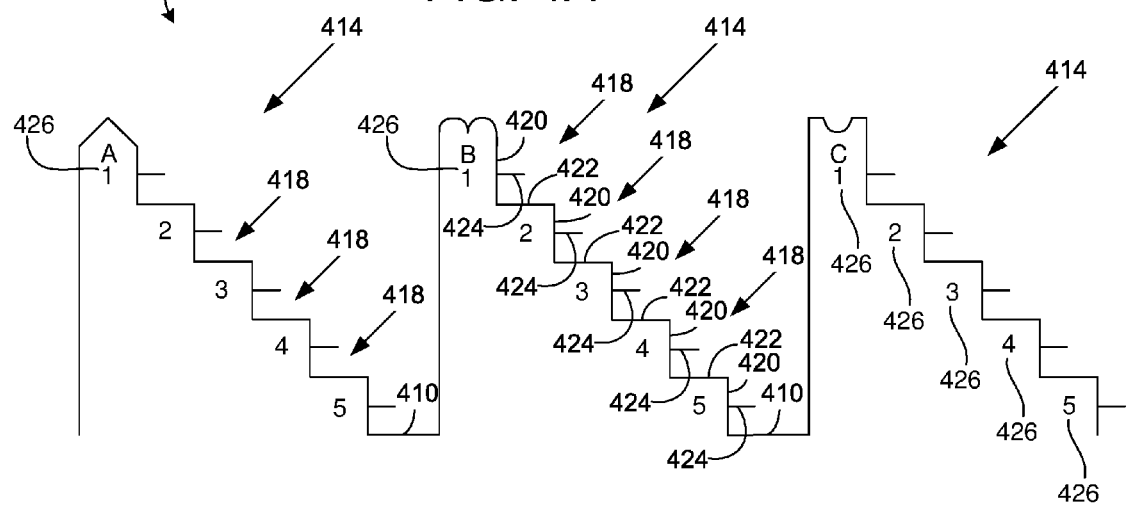

FIG. 4A shows a TEM grid 402 that includes a body 404 having an outer edge in the form of a partial circle 408 having a diameter of about three millimeters and an inner edge 410 within the outer edge formed by a partial chord of the partial circle 408. Multiple posts 414 extend from the inner edge 410. FIG. 4B shows an enlarged view of three posts 414. As depicted, the posts 414 in this embodiment are spaced along the inner edge with their bases separated by intervening portions of inner edge 410. Each post has steps 418 formed from a vertical edge 420 and a horizontal edge 422 substantially parallel to the inner edge 410. The vertical edge 420 provides a place for attaching a sample 424 for thinning using a focused ion beam system and/or for viewing on a transmission electron microscope.

Each post 414 optionally has a different geometric shape at the top for ease of automatic machine identification and each step 418 can also have an identifier 426. In one embodiment, vertical edge 420 and a horizontal edge 422 are each 50 µm long, which provides ample room to place a sample, which is typically about 10 µm wide and about 5 µm tall. Indicia, such as simplified letter "A", "B", and "C" at the top of each staircase could be used to aid in identification of the sample, with the steps consecutively numbers, for example, 1, 2, 3, 4, and 5. The designator for each individual step can be written on the grid, or just understood by the position. The staircase could be one-sided as shown, or double sided, that is, pyramid shaped. Because of the orientation of the sample after removal in some extract processes, it is easier to weld to one side of the post than to the other side.

Figure 6:
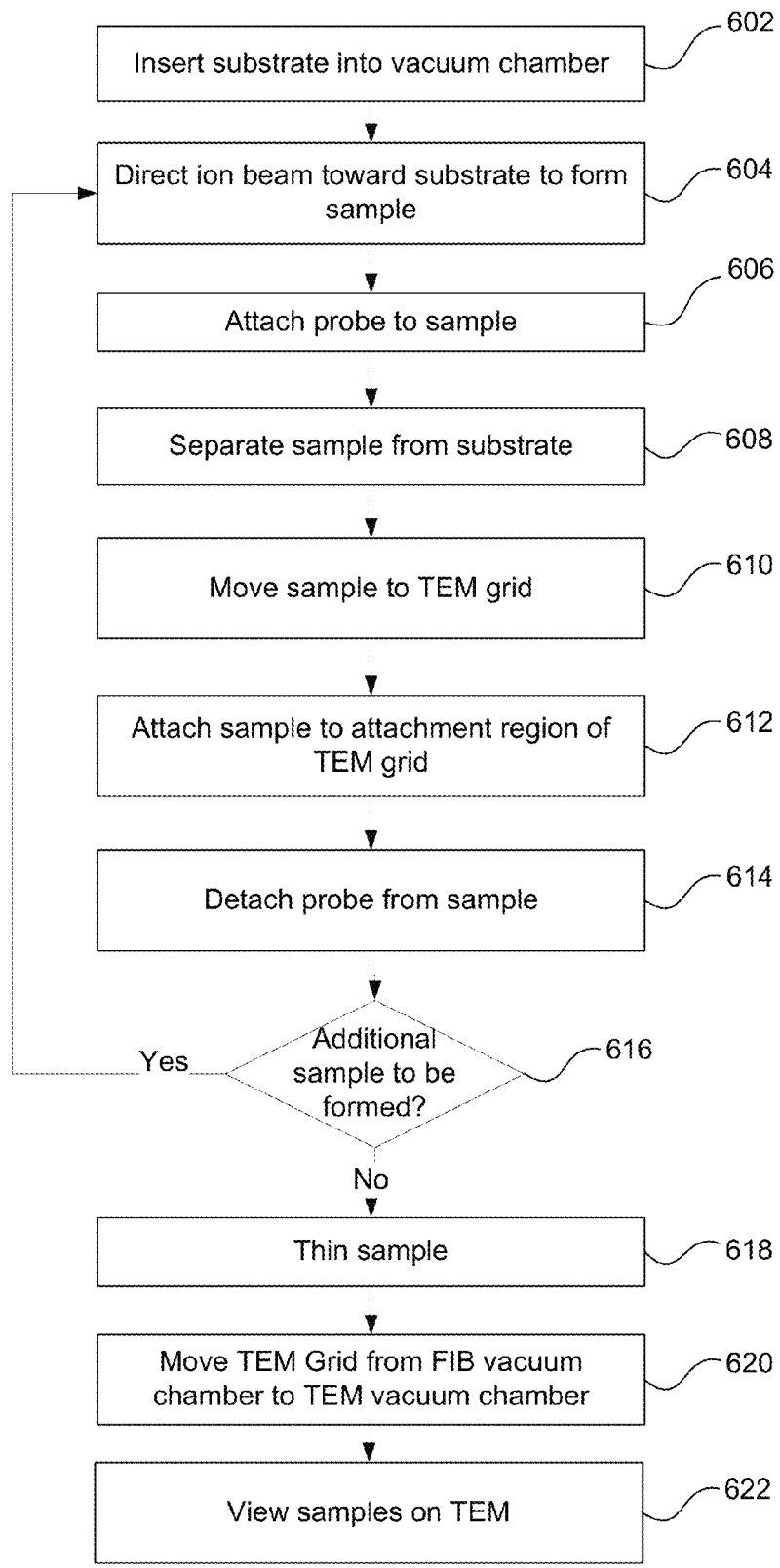
FIG. 6 is a flow chart showing a method of fabrication sample for transmission electron microscope.

FIG. 6 is a flow chart showing a method of preparing multiple samples for observation on a TEM. In step 602, a user inserts a sample substrate into a vacuum chamber. In step 604, a focused ion beam is directed toward the sample substrate to form a sample. Prior to separating the sample from the substrate, a probe is attached to the sample in step 606. In step 608, the sample is severed from the substrate. In step 610, the probe with the first thin sample attached is moved to the TEM grid, such as the one described in FIG. 4. In step 612, the first thin sample is attached to the TEM grid on one of the multiple steps of a post. In step 614, the probe is detached from the sample, leaving it on the TEM grid.

In decision block 616, it is determined whether or not there are additional samples to be formed. If so, the process repeats at step 604. As each sample is formed and removed from the substrate, each sample is attached to a vertical edge 420 of a different one of the steps 418 of a post 414 until all the steps are filled. The order in which the steps are filled can be varied. For example, a sample can be extracted, moved to grid 400 and stored at position A1. A second sample is extracted and moved to grid 400 and stored at position A2. A third sample is extracted and moved to grid 400 and stored at position A3, and so forth to fill Post A. Next, a sample is extracted and welded to the first step of Post B. Then, a sample is extracted and welded to step B2, then B3 and so forth. Then Post C can be filled in the same way. Eventually, all the steps on all the posts can be filled. Alternatively, the top steps on each post could be filled and then the next step down. The example grid 400 can hold 15 samples mounted on the stairs and 18 samples if both sides of the post are used. Other embodiments can have different numbers of posts and different numbers of steps of each post. Different posts may have different numbers of steps and the steps may differ in size and pitch. A TEM grid with stair steps on both sides can hold even more samples.

After all the desired samples are formed and moved to the TEM grid, the samples on the TEM grid are thinned in step 618 with the focused ion beam. The order of processing can be changed. For example, multiple thin samples could be partly formed by repeating step 604 and then each of the partly formed samples can be severed, moved to the TEM grid, and attached to the TEM grid by repeating steps 606 to step 614. The samples can be thinned before severing from the sample, after each thin sample is attached to the TEM grid, or after all the thin samples have been attached to the TEM grid.

In step 620, the TEM grid is moved to a TEM and in step 622, the samples are imaged on the TEM. Steps 604 to 618 can be partly or completely automated.

Figure 7:
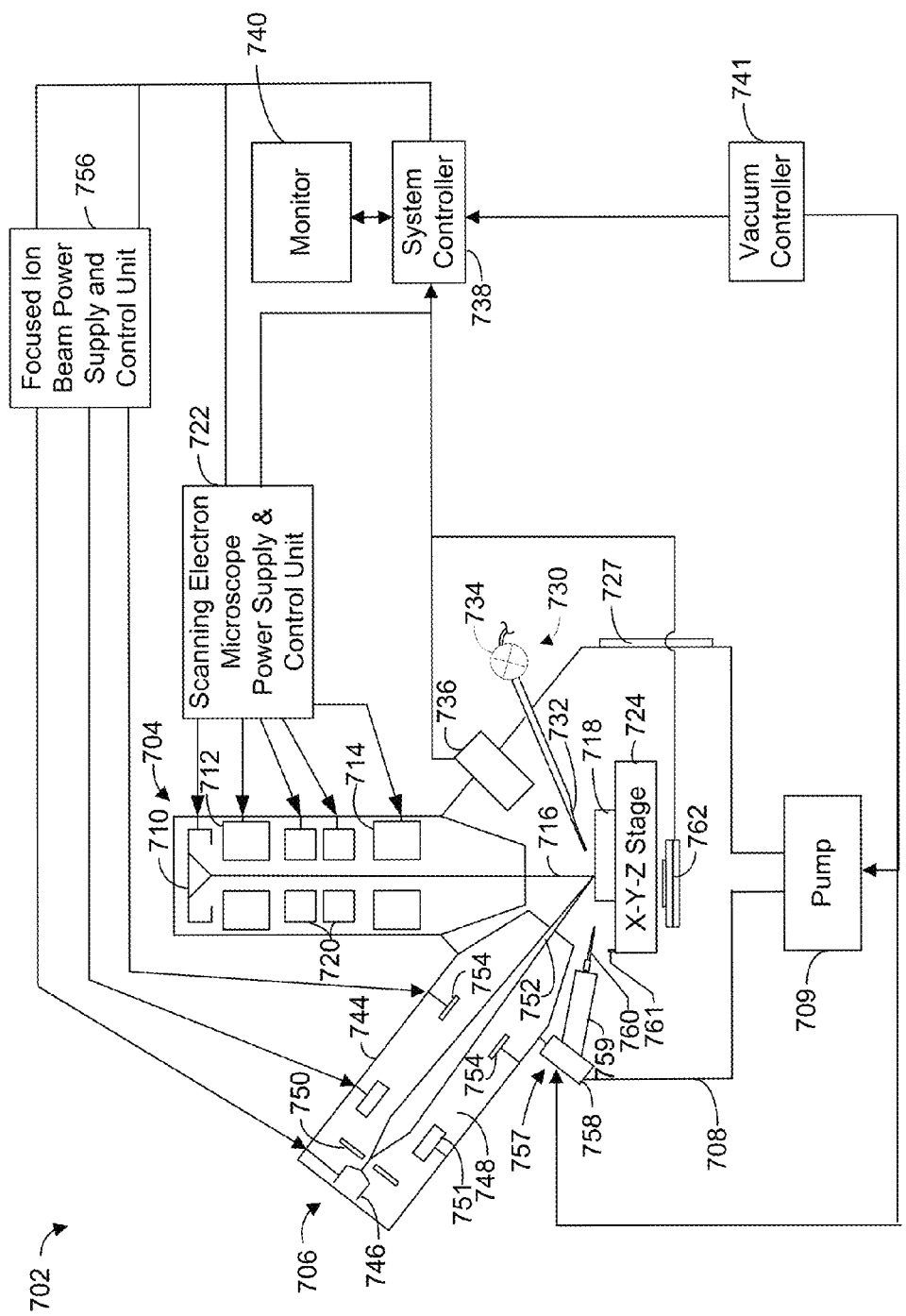
FIG. 7 shows a dual beam system that can be used to prepare samples for TEM viewing.

FIG. 7 depicts of an exemplary dual beam SEM/FIB system 702 that is equipped to form samples and move them to a TEM grid. Suitable dual beam systems are commercially available, for example, from FEI Company, Hillsboro, Oreg., the assignee of the present application. While an example of suitable hardware is provided below, the invention is not limited to being implemented in any particular type of hardware.

Dual beam system 702 has a vertically mounted electron beam column 704 and a focused ion beam (FIB) column 706 mounted at an angle of approximately 52 degrees from the vertical on an evacuable specimen chamber 708. The specimen chamber may be evacuated by pump system 709, which typically includes one or more, or a combination of, a turbomolecular pump, oil diffusion pumps, ion getter pumps, scroll pumps, or other known pumping means.

The electron beam column 704 includes an electron source 710, such as a Schottky emitter or a cold field emitter, for producing electrons, and electron-optical lenses 712 and 714 forming a finely focused beam of electrons 716. Electron source 710 is typically maintained at an electrical potential of between 500 V and 30 kV above the electrical potential of a work piece 718, which is typically maintained at ground potential.

Thus, electrons impact the work piece 718 at landing energies of approximately 500 eV to 30 keV. A negative electrical potential can be applied to the work piece to reduce the landing energy of the electrons, which reduces the interaction volume of the electrons with the work piece surface, thereby reducing the size of the nucleation site. Work piece 718 may comprise, for example, a semiconductor device, microelectromechanical system (MEMS), data storage device, or a sample of material being analyzed for its material characteristics or composition. The impact point of the beam of electrons 716 can be positioned on and scanned over the surface of a work piece 718 by means of deflection coils 720. Operation of lenses 712 and 714 and deflection coils 720 is controlled by scanning electron microscope power supply and control unit 722. Lenses and deflection unit may use electric fields, magnetic fields, or a combination thereof.

Work piece 718 is on movable stage 724 within specimen chamber 708. Stage 724 can preferably move in a horizontal plane (X-axis and Y-axis) and vertically (Z-axis) and can tilt approximately sixty (60) degrees and rotate about the Z-axis. A door 727 can be opened for inserting work piece 718 onto X-Y-Z stage 724 and also for servicing an internal gas supply reservoir (not shown), if one is used. The door is interlocked so that it cannot be opened if specimen chamber 708 is evacuated.

Mounted on the vacuum chamber are one or more gas injection systems (GIS) 730. Each GIS may comprise a reservoir (not shown) for holding the precursor or activation materials and a needle 732 for directing the gas to the surface of the work piece. Each GIS further comprises means 734 for regulating the supply of precursor material to the work piece. In this example the regulating means are depicted as an adjustable valve, but the regulating means could also comprise, for example, a regulated heater for heating the precursor material to control its vapor pressure.

When the electrons in the electron beam 716 strike work piece 718, secondary electrons, backscattered electrons, and Auger electrons are emitted and can be detected to form an image or to determine information about the work piece. Secondary electrons, for example, are detected by secondary electron detector 736, such as an Everhart-Thornley detector, or a semiconductor detector device capable of detecting low energy electrons. A STEM detector 762, located beneath the TEM grid 761 and the stage 724 allows detection of electrons transmitted though the sample. Stage 724 and TEM grid 761 can be configured so that detector 762 can collect electrons that are transmitted through a sample mounted on the TEM grid. Signals from the detectors 736 and 762 are provided to a system controller 738. Said controller 738 also controls the deflector signals, lenses, electron source, GIS, stage and pump, and other items of the instrument. Monitor 740 is used to display user controls and an image of the work piece using the signal The chamber 708 is evacuated by pump system 709 under the control of vacuum controller 741. The vacuum system provides within chamber 708 a vacuum of approximately 7×10-6 mbar. When a suitable precursor or activator gas is introduced onto the sample surface, the chamber background pressure may rise, typically to about 5×10-5 mbar.

Focused ion beam column 706 comprises an upper neck portion 744 within which are located an ion source 746 and a focusing column 748 including extractor electrode 750 and an electrostatic optical system including an objective lens 751. Ion source 746 may comprise a liquid metal gallium ion source, a plasma ion source, a liquid metal alloy source, or any other type of ion source. The axis of focusing column 748 is tilted 52 degrees from the axis of the electron column. An ion beam 752 passes from ion source 746 through focusing column 748 and between electrostatic deflectors 754 toward work piece 718.

FIB power supply and control unit 756 provides an electrical potential at ion source 746. Ion source 746 is typically maintained at an electrical potential of between 1 kV and 60 kV above the electrical potential of the work piece, which is typically maintained at ground potential. Thus, ions impact the work piece at landing energies of approximately 1 keV to 60 keV. FIB power supply and control unit 756 is coupled to deflection plates 754 which can cause the ion beam to trace out a corresponding pattern on the upper surface of work piece 718. In some systems, the deflection plates are placed before the final lens, as is well known in the art. Beam blanking electrodes (not shown) within ion beam focusing column 748 cause ion beam 752 to impact onto blanking aperture (not shown) instead of work piece 718 when a FIB power supply and control unit 756 applies a blanking voltage to the blanking electrode.

The ion source 746 typically provides a beam of singly charged positive gallium ions that can be focused into a sub one-tenth micrometer wide beam at work piece 718 for modifying the work piece 718 by ion milling, enhanced etch, material deposition, or for imaging the work piece 718.

A micromanipulator 757, such as the AutoProbe 200™ from Omniprobe, Inc., Dallas, Tex., or the Model MM3A from Kleindiek Nanotechnik, Reutlingen, Germany, can precisely move objects within the vacuum chamber. Micromanipulator 757 may comprise precision electric motors 758 positioned outside the vacuum chamber to provide X, Y, Z, and theta control of a portion 759 positioned within the vacuum chamber. The micromanipulator 757 can be fitted with different end effectors for manipulating small objects. In the embodiments described herein, the end effector is a thin probe 760. A micromanipulator (or microprobe) can be used to transfer a TEM sample (which has been freed from a substrate, typically by an ion beam) to a TEM grid in a TEM sample holder 761 for analysis. Stage 724 can also include mounted thereon a flip stage (not shown) as described for example in U.S. Pat. Pub. No. 20040144924 of Asselbergs et al. for "Method for the Manufacture and Transmissive Irradiation of a Sample, and Particle-optical System," which is owned by the applicant of the present invention and which is hereby incorporated by reference. Mounting the TEM grid on the flip stage allows the orientation of the TEM grid to be changed and, with rotation of the stage, allows the sample can be mounted in a desired orientation.

System controller 738 controls the operations of the various parts of dual beam system 702. Through system controller 738, a user can cause ion beam 752 or electron beam 716 to be scanned in a desired manner through commands entered into a conventional user interface (not shown). Alternatively, system controller 738 may control dual beam system 702 in accordance with programmed instructions. FIG. 7 is a schematic representation, which does not include all the elements of a typical dual beam system and which does not reflect the actual appearance and size of, or the relationship between, all the elements.

FIGS. 8A and 8B show, respectively, a front view and a rear view of a preferred embodiment of a TEM grid 802. The TEM grid 802 includes a body 804 having an outer edge 808 and an inner edge 810 within the boundary define by the outer edge 808. Multiple posts 814 extend from the inner edge 810. Each post has steps 818 formed from a vertical edge normal to inner edge 810 and a horizontal edge substantially parallel to the inner edge 810. The vertical edge provides a place for attaching a sample for thinning using a focused ion beam system and/or for viewing on a transmission electron microscope. Each post 814 optionally has a different geometric shape at the top for ease of automatic machine identification and each step 818 can also have an identifier. Optional orientation indicator 820 of the TEM grid 802 allows the user to easily determine which side of the TEM grid 802 is face up.

While the features on the posts of the grids have been referred to as "steps," the term "step" does not mean that the various edges need to be parallel and/or perpendicular to the base line from which the post extends. Any jagged post edge that provides multiple positions for mounting samples can use be used. For example, the post edge may include first portions that are normal to the base line and second angled portions that are not parallel to the baseline connecting the first edge portions. Alternatively, the samples are typically attached to the portions that are normal to the base line. Alternatively, the post edge may include first portions that are parallel to the base line and second angled portions connecting the lines that are not parallel to the baseline. The post can include a jagged etch on one side and a straight edge on the second side, or jagged edges on both sides. The jagged edges are composed of edge segments, each separated from another edge segment by a vertex. Each segment comprises a sample mounting region. In some embodiments, there are more than three edge segments, preferably more than four, and more preferably five or more edge segments on one jagged edge of the post, with each edge segment comprising a sample mounting region.

The TEM grid can provide 9 or more, 12 or more, or 15 or more sample positions on a single TEM grid. For example, the grid can contain two or more posts, each with one or more jagged edges. Each jagged edge can provide more than 3, more than 4, more than 5, or more than 6 sample mounting regions. Embodiments of TEM grids are constructed with setbacks as shown on FIG. 5 to facilitate attaching the sample at the sample positions.

Some embodiments of the invention provide a TEM grid for a transmission electron microscope, comprising: a holder body; at least one attachment element attached to the holder body for attaching multiple thin samples prepared for viewing on a TEM, the attachment element having a base and including at least two steps to which the thin sample can be attached, the steps located at different distance from the base.

In some embodiments, the at least one attachment element includes at least 2 attachment elements, each of the at least two attachment elements including at least two steps.

In some embodiments, the at least one attachment element includes at least three steps.

In some embodiments, the at least one attachment element includes at least three attachment elements and in which each of the at least three attachment elements includes at least three steps.

In some embodiments, the holder body is composed of a conductive material.

In some embodiments, the at least two steps are one the same side of the attachment element.

In some embodiments, the TEM grid includes identifying marks identifying each attachment element.

In some embodiments, the TEM grid of includes identifying marks identifying each of the at least two steps.

In some embodiments, the attachment element has a base and in which the multiple steps begin at different distance from the base of the attachment element.

In some embodiments, the TEM grid is stamped, etched, or laser-cut during its manufacturing process.

In some embodiments, in which the attachment element includes a setback at the at least two steps to which the thin sample can be attached.

Some embodiments of the invention provide a method of preparing samples for viewing in a transmission electron microscope, the method comprising:
directing a focused ion beam toward a substrate to severing a first sample from the substrate;
attaching the first sample to a manipulator;

moving the first sample to a tem grid, the TEM grid including a body and an attachment structure, the attachment structure including multiple steps;

attaching the first sample to a first one of the multiple steps on the attachment structure;

directing a focused ion beam toward a substrate to sever a second sample from the substrate; and attaching the second sample to a second one of the multiple steps on the attachment structure.

In some embodiments, the method further comprises directing an electron beam toward the first sample to form a transmission electron image of the first sample and directing an electron beam toward the second sample to form a transmission electron image of the second sample.

In some embodiments, attaching the first sample to a first one of the multiple steps on the attachment structure includes directing a focused ion beam to deposit material to attached the first sample to the first one of the multiple steps; and attaching the second sample to a second one of the multiple steps on the attachment structure includes directing a focused ion beam to deposit material to attach the second sample to the second one of the multiple steps.

In some embodiments, attaching the first sample to a manipulator or attaching the second sample to a manipulator includes attaching the first sample or the second sample to the manipulator by beam induced deposition, sputter deposition, an adhesive, or electrostatic attraction.

In some embodiments, the method further comprises thinning the first sample or the second sample using the ion beam after the first sample or second sample is attached to the TEM grid.

In some embodiments, the method further comprises automatically recognizing an identifying mark using machine vision.

Some embodiments of the invention provide a TEM grid comprising:

a body having an outer edge in the form of a partial circle having a diameter of about three millimeters and an inner edge within the outer edge formed by a chord of the partial circle; and at least one post extending from the inner edge, the at least one post having at least one jagged edge forming multiple sample mounting positions for attachment of thin samples for viewing on a transmission electron microscope, each sample position on a different line segment.

In some embodiments, at least one jagged edge forms at least three sample mounting positions.

In some embodiments, the at least one post includes one straight edge and on jagged edge including at least three sample mounting positions.

In some embodiments, the at least one post includes at least three posts, each post including a jagged edge on one side of the post.

In some embodiments, the at least one post comprising multiple posts, each of the multiple posts including at least one jagged edge.

In some embodiments, the TEM grid further comprises identifying marks identifying each of the multiple sample mounting positions.

In some embodiments, the TEM grid is stamped, etched, or laser-cut during its manufacturing process.

A preferred method or apparatus of the present invention has many novel aspects, and because the invention can be embodied in different methods or apparatuses for different purposes, not every aspect need be present in every embodiment. Moreover, many of the aspects of the described embodiments may be separately patentable. The invention has broad applicability and can provide many benefits as described and shown in the examples above. The embodiments will vary greatly depending upon the specific application, and not every embodiment will provide all of the benefits and meet all of the objectives that are achievable by the invention.

It should be recognized that embodiments of the present invention can be implemented via computer hardware, a combination of both hardware and software, or by computer instructions stored in a non-transitory computer-readable memory. The methods can be implemented in computer programs using standard programming techniques—including a non-transitory computer-readable storage medium configured with a computer program, where the storage medium so configured causes a computer to operate in a specific and predefined manner—according to the methods and figures described in this Specification. Each program may be implemented in a high level procedural or object oriented programming language to communicate with a computer system. However, the programs can be implemented in assembly or machine language, if desired. In any case, the language can be a compiled or interpreted language. Moreover, the program can run on dedicated integrated circuits programmed for that purpose.

Further, methodologies may be implemented in any type of computing platform, including but not limited to, personal computers, mini-computers, main-frames, workstations, networked or distributed computing environments, computer platforms separate, integral to, or in communication with charged particle tools or other imaging devices, and the like. Aspects of the present invention may be implemented in machine readable code stored on a non-transitory storage medium or device, whether removable or integral to the computing platform, such as a hard disc, optical read and/or write storage mediums, RAM, ROM, and the like, so that it is readable by a programmable computer, for configuring and operating the computer when the storage media or device is read by the computer to perform the procedures described herein. Moreover, machine-readable code, or portions thereof, may be transmitted over a wired or wireless network. The invention described herein includes these and other various types of non-transitory computer-readable storage media when such media contain instructions or programs for implementing the steps described above in conjunction with a microprocessor or other data processor. The invention also includes the computer itself when programmed according to the methods and techniques described herein.

Computer programs can be applied to input data to perform the functions described herein and thereby transform the input data to generate output data. The output information is applied to one or more output devices such as a display monitor. In preferred embodiments of the present invention, the transformed data represents physical and tangible objects, including producing a particular visual depiction of the physical and tangible objects on a display.

In the following discussion and in the claims, the terms "including" and "comprising" are used in an open-ended fashion, and thus should be interpreted to mean "including, but not limited to . . . . " To the extent that any term is not specially defined in this specification, the intent is that the term is to be given its plain and ordinary meaning. The accompanying drawings are intended to aid in understanding the present invention and, unless otherwise indicated, are not drawn to scale. Particle beam systems suitable for carrying out the present invention are commercially available, for example, from FEI Company, the assignee of the present application.

Although the present invention and its advantages have been described in detail, it should be understood that various changes, substitutions and alterations can be made to the embodiments described herein without departing from the spirit and scope of the invention as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, compositions of matter, means, methods, or steps, presently existing or later to be developed that perform substantially the same function or achieve substantially the same result as the corresponding embodiments described herein may be utilized according to the present invention. Accordingly, the appended claims are intended to include within their scope such processes, machines, manufacture, compositions of matter, means, methods, or steps.

We claim as follows:

1. A TEM grid for a transmission electron microscope, comprising:
   a holder body having an outer edge and an inner edge;
   multiple attachment elements attached to the holder body, each respective attachment element adapted for attaching multiple thin samples prepared for viewing on a TEM, each respective attachment element having a base attached to the holder body and having at least two steps, each step adapted to receive attachment of a respective one of the thin samples, the steps of each respective attachment element located at different distances from the base;
   wherein each respective attachment element has an opposite side from the at least two steps, the opposite side including no steps and further adapted to receive a respective one of the thin samples attached at a desired distance from a bulk of the TEM grid, adapted to permit fine energy dispersive x-ray spectroscopy analysis of the sample with very low redeposition thinning of the sample.

2. The TEM grid of claim 1 in which the multiple attachments elements are spaced along the inner edge with their bases separated by intervening portions of the inner edge.

3. The TEM grid of claim 1 in which each respective attachment element includes at least three steps.

4. The TEM grid of claim 1 including at least three attachment elements, and in which each of the at least three attachment elements includes at least three steps.

5. The TEM grid of claim 1 in which the holder body is composed of a conductive material.

6. The TEM grid of claim 1 in which the at least two steps are on the same side of each respective attachment element, and the side with no steps is oriented in the same direction for each respective attachment element.

7. The TEM grid of claim 1 further comprising identifying marks identifying each attachment element.

8. The TEM grid of claim 1 further comprising identifying marks identifying each of the at least two steps of each respective attachment element.

9. The TEM grid of claim 1 in which each step is adapted to receive attachment of a respective one of the thin samples by receiving a focused ion beam to deposit material to attach the respective one of the thin samples.

10. The TEM grid of claim 1 further comprising a marker on the holder body indicating in which direction the sides of the attachment elements having no steps are facing.

11. The TEM grid of claim 1 in which each of the attachment elements includes a setback at the at least two steps to which the thin sample can be attached.

12. A method of preparing samples for viewing in a transmission electron microscope, comprising:
    directing a focused ion beam toward a substrate to severing a first sample from the substrate;
    attaching the first sample to a manipulator;
    moving the first sample to a TEM grid, the TEM grid including a body and two or more attachment structures, the attachment structures each including multiple steps and each having a top end with a different shape from the other attachment structures;
    identifying a first one of the attachment structures by its top end shape and attaching the first sample to a selected one of the multiple steps on the first one of the two or more attachment structures;
    directing a focused ion beam toward a substrate to sever a second sample from the substrate; and
    identifying a second one of the attachment structures by its top end shape and attaching the second sample to a selected one of the multiple steps on the second of one of the two or more attachment structures.

13. The method of claim 12 further comprising directing an electron beam toward the first sample to form a transmission electron image of the first sample and directing an electron beam toward the second sample to form a transmission electron image of the second sample.

14. The method of claim 12 in which:
    attaching the first sample to the selected one of the multiple steps on the first attachment structure includes directing a focused ion beam to deposit material to attached the first sample to the selected one of the multiple steps; and
    attaching the second sample to the selected one of the multiple steps on the second attachment structure includes directing a focused ion beam to deposit material to attach the second sample to the selected one of the multiple steps.

15. The method of claim 12 in which attaching the first sample to a manipulator or attaching the second sample to a manipulator includes attaching the first sample or the second sample to the manipulator by beam induced deposition, sputter deposition, an adhesive, or electrostatic attraction.

16. The method of claim 12 further comprising thinning the first sample or the second sample using the ion beam after the first sample or second sample is attached to the TEM grid.

17. The method of claim 12 further comprising automatically recognizing an identifying mark specific to the selected one of the multiple the first attachment structure using machine vision.

18. A TEM grid comprising:
    a body having an outer edge in the form of a partial circle having a diameter of about three millimeters and an inner edge within the outer edge formed by a chord of the partial circle; and
    at least two posts extending from the inner edge, the at least one post having at least one jagged edge forming multiple sample mounting positions adapted for attachment of thin samples for viewing on a transmission electron microscope, each sample position on a different line segment, the at least two posts each having a top end with a different shape from the other posts.

19. The TEM grid of claim 18 in which the at least one jagged edge forms at least three sample mounting positions.

20. The TEM grid of claim 18 in which the at least one post includes one straight edge, and one jagged edge including at least three sample mounting positions.

21. The TEM grid of claim 18 in which the at least one post includes at least three posts, each post including a jagged edge on one side of the post.

22. The TEM grid of claim 18 in which the at least one post comprises multiple posts separated by intervening portions of the inner edge, and which respectively include at least one jagged edge forming multiple sample mounting positions adapted for attachment of thin samples for viewing on the transmission electron microscope.

23. The TEM grid of claim 18 further comprising identifying marks identifying each of the multiple sample mounting positions.

24. The TEM grid of claim 18 in which the at least one post comprises multiple posts separated by intervening portions of the inner edge, and which respectively include at least two jagged edges each forming multiple sample mounting positions adapted for attachment of thin samples for viewing on the transmission electron microscope.

\* \* \* \* \*